US008512222B2

(12) United States Patent  (10) Patent No.: US 8,512,222 B2
Millman  (45) Date of Patent: Aug. 20, 2013

(54) SYSTEM AND METHOD FOR REORIENTING AND DECREASING PATIENT ANXIETY IN A MEDICAL FACILITY

(76) Inventor: Bruce Ian Millman, West Bloomfield, MI (US)

( * ) Notice: Subject to any disclaimer, the term of this patent is extended or adjusted under 35 U.S.C. 154(b) by 87 days.

(21) Appl. No.: 13/279,907

(22) Filed: Oct. 24, 2011

(65) Prior Publication Data

US 2013/0102836 A1  Apr. 25, 2013

(51) Int. Cl.
*A61M 21/00* (2006.01)
(52) U.S. Cl.
USPC ............................................. 600/27; 725/34
(58) Field of Classification Search
USPC ........... 600/26–28; 725/34, 37, 78; 128/897, 128/898
See application file for complete search history.

(56) References Cited

U.S. PATENT DOCUMENTS

| | | | |
|---|---|---|---|
| 5,517,392 A | 5/1996 | Rousso et al. | |
| 6,339,410 B1 | 1/2002 | Milner et al. | |
| 2003/0097351 A1 | 5/2003 | Rothschild et al. | |
| 2008/0071573 A1* | 3/2008 | Owens et al. | 705/2 |
| 2009/0076856 A1* | 3/2009 | Darby et al. | 705/3 |
| 2009/0096743 A1 | 4/2009 | DalPorto et al. | |
| 2009/0326979 A1* | 12/2009 | Ryan | 705/2 |
| 2010/0115548 A1* | 5/2010 | Leyvi | 725/34 |
| 2010/0312042 A1* | 12/2010 | Anderson et al. | 600/28 |
| 2011/0126236 A1 | 5/2011 | Arrasvuori et al. | |
| 2011/0214234 A1 | 9/2011 | Herman | |

OTHER PUBLICATIONS

Veterinary Economics: Slideshow: Samples for exam-room digital picture frames, Feb. 1, 2009.
Mary Beth Happ, Ph.D., R.N. et al., AAC in the ICU: Critical Issues and Preliminary Research, Presentation at the Annual ASHA Convention, Nov. 2003.
MB Happ et al., Use of Electronic Communication Aids in Medical Intensive Care, May 2003.
Communication—an inalienable right, MacAulay F. Ninewells Hospital, Dundee, Scotland, UK, Speech Lang Ther Pract Winter 2002, p. 12-4.
Ondria C. Gleason, M.D., Delirium, American Family Physician, Mar. 1, 2003, vol. 67. No. 5, pp. 1027-1034.
CHATPC-II, Infogrip, Inc., 2003.
International Searching Authority, International Search Report and the Written Opinion for corresponding PCT/US2012/58890 mailed Mar. 5, 2013.

\* cited by examiner

*Primary Examiner* — Charles A Marmor, II
*Assistant Examiner* — Carrie R Dorna
(74) *Attorney, Agent, or Firm* — Brooks Kushman P.C.

(57) ABSTRACT

A computer system for reorienting, reducing anxiety, and/or reducing delirium risk of a patient in a hospital is provided. The computer has a central processing unit (CPU) for executing machine instructions for a passive and active module and a memory for storing the machine instructions. The machine instructions implement functions when executed by the CPU. Patient-specific content is inputted into the CPU. The system then communicates the patient-specific content from the CPU to the patient by displaying and looping the patient-specific content such that any point of the loop of the patient-specific content helps reorient and reduce anxiety and delirium risk.

20 Claims, 6 Drawing Sheets

SYSTEM AND METHOD FOR REORIENTING AND DECREASING PATIENT ANXIETY IN A MEDICAL FACILITY

TECHNICAL FIELD

This application relates to a system and method for reorienting, decreasing anxiety, and/or reducing delirium risk in a patient in a medical facility.

BACKGROUND

The mental condition of a hospitalized patient can pose serious therapeutic challenges to medical care providers. Often, due to underlying medical conditions, the patient may exhibit serious and potentially life threatening psychological manifestations such as anxiety or delirium. Anxiety may be defined as a "state of intense apprehension or fear of real or imagined danger." Delirium may be defined as a "state of marked confusion" that can be provoked by an underlying medical condition. Both anxiety and delirium can occur in hospitalized patients in an intensive care unit (ICU), progressive "step-down" medical floors, and general medical floors.

Many medical conditions can provoke significant anxiety. A pertinent example in the ICU setting is as follows: an elderly nursing home patient overdoses on pain medication, develops unconsciousness, and then aspirates food contents into the trachea and lung. The patient is emergently brought by emergency medical services (EMS) to the nearest emergency room (ER). This patient may require intubation and be placed on a mechanical ventilator (i.e., breathing machine) to facilitate breathing and oxygen/carbon dioxide exchange. During intubation, a tube is inserted through the vocal cords preventing the patient from speaking. In addition, the patient is usually hand restrained to prevent accidentally pulling the life-sustaining tube out of her mouth. The above condition necessitates the patient to have a bed position that has the patient invariably looking up at a white-tiled ceiling or the like. In addition, ambient noise from other ICU patients' noise, ventilator/cardiac alarm noise, and conversation noise also contribute to a less than calming and peaceful "healing" environment. Many studies have shown that a typical ICU bed can have noise >75 db. This can lead to sleep deprivation over several days, which can result in altered conscious states and further anxiety and delirium.

Nursing and other medical staff personnel may make "bedside" attempts to reorient and calm a patient, but these good-intentioned efforts often do not lead to the desired result of a calm, cooperative, and oriented patient in the ICU or other hospital floors. Furthermore, these efforts are time-consuming, costly, and often ineffective due to staffing constraints and priorities. In addition, often there is a language barrier between the patient and the nurse/medical personnel potentially leading to significant more patient anxiety and confusion. The above factors can lead to a recurrent cycle of anxiety and delirium that is very difficult to break on a practical basis. As a consequence, nursing and medical staff personnel are unfortunately then necessitated to use intravenous (IV) anti-anxiety and anti-psychotic medications that have potential significant side effects. These side effects often include hypotension, lethal cardiac arrhythmias, electrolyte imbalance, and even further confusion paradoxically. In addition, several ICU peer-reviewed, evidence-based medical studies and clinical trials have demonstrated that unnecessary sedation medications lead to significant increased length of stay in the ICU, prolonged time on life support breathing machines, and significantly more costs in the thousands of dollars. Unfortunately, due to health care systems' limitations on nursing to patient staffing ratio and hospital financial constraints, constant "bedside" care to minimize anxiety or delirium risk factors have not been optimal.

If a patient improves in the ICU or other medical floor, the patient can potentially become more interactive with their environment and staff. At this point, the patient can be fully aware and cooperative with others. Unfortunately, many illnesses and just being in a hospital setting can lead to an anxious or even depressed mood. Often patients are spending countless hours waiting for tests to be done. Without connections to outside the hospital environment, patients can become bored, isolated, and detached.

SUMMARY

In one embodiment, a computer system is provided for a patient in a medical facility comprising a computer having a central processing unit (CPU) for executing machine instructions comprising a passive module and a memory for storing machine instructions that are to be executed by the CPU. The machine instructions when executed by the CPU implement the following functions: receiving patient-specific content, formatting the patient-specific content into content pages to form a looped content segment, and transmitting the looped content segment for display to the patient.

In another embodiment, a computer viewing apparatus is provided for connection to a hospital bed. The apparatus comprises a repositionable flexible arm assembly including conductive wires contained therein to connect a computer to a power source, a flexible spine at least partially surrounding the wires that includes a number of interconnected and universally rotatable members, and a sleeve engaging an outer surface of each of the rotatable members. The apparatus further comprises an anchoring member at a first end of the flexible arm that attaches the flexible arm to the hospital bed, and a connection member at a second end of the flexible arm that attaches the computer to the flexible arm.

In another embodiment, a method is provided for reorienting, reducing anxiety and/or reduce risk factors for delirium in a patient in a medical facility in a state of intermittent or decreased consciousness by displaying content to the patient on a screen that is connected to a bed on which the patient is located. The method comprises the steps of transmitting patient-specific content to a display screen including an identification of the patient and a medical status of the patient, and looping the patient-specific content in a display loop to reorient, reduce anxiety, and reduce risk factors for delirium in the patient.

DETAILED DESCRIPTION

Detailed embodiments of the present invention are disclosed herein. It is to be understood that the disclosed embodiments are merely exemplary of the invention that may be embodied in various and alternative forms. The figures are not necessarily to scale, and some features may be exaggerated or minimized to show details of particular components. Therefore, specific structural and functional details disclosed by the Applicant are not to be interpreted as limiting, but merely as a representative basis for teaching one skilled in the art to variously employ the present invention.

The embodiments described herein relate to a computer system, apparatus, and method for reorienting, decreasing anxiety, and/or reducing delirium risk throughout the course of a patient's hospital stay. Offering a patient specific, non-pharmacological method for reorienting and decreasing patient anxiety may avoid the potentially significantly costly and life threatening effects of medications. In the ICU setting, for example, a passive approach to reorienting the patient and/or improving their anxiety and delirium may be taken. As a patient recovers, embodiments may provide a more interactive/active approach to improving the patient's anxiety, boredom, and detachment from the outside hospital environment, as well as enhancing the overall patient experience.

Figure 1A:
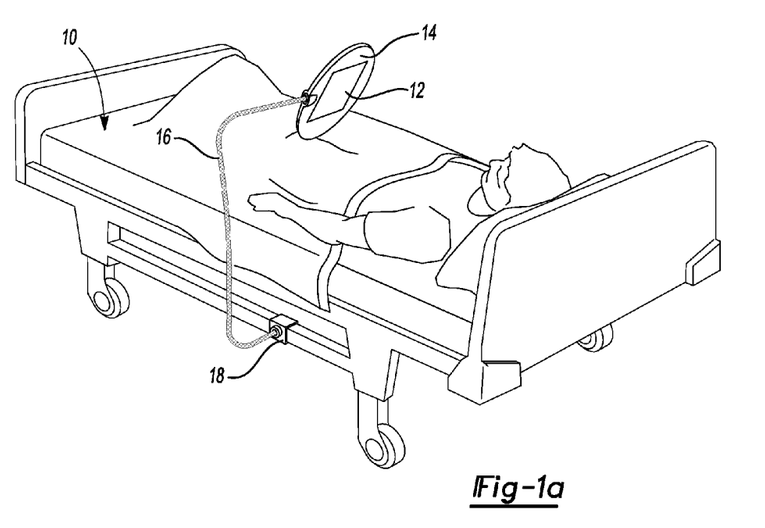
FIGS. 1a and 1b are perspective views of a hospital bed with a computer to facilitate reorientation and reduce anxiety and delirium risk in a patient, wherein the computer is attached to the hospital bed by a flexible arm, and the computer is shown in a first position (FIG. 1a) with the patient in a prone position and a second position (FIG. 1b) with the patient in an upright position.
Figure 1B:
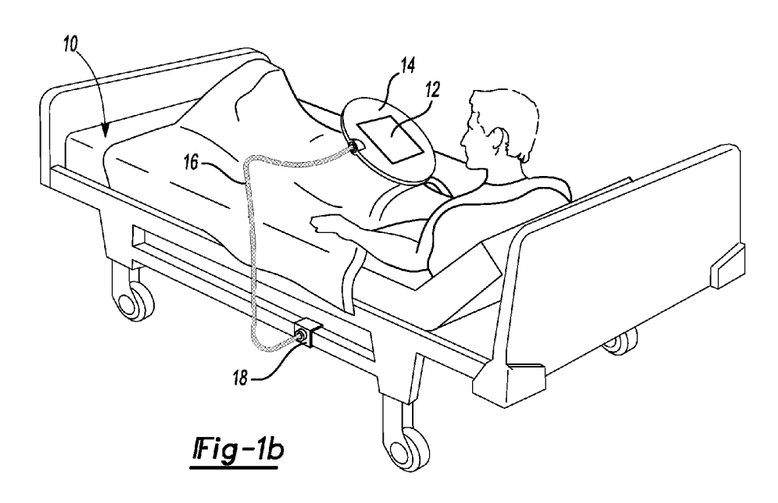

Referring to FIGS. 1a and 1b, a hospital bed 10 is depicted for a patient to rest on while being treated at a hospital or other medical facility. A computer 12 is attached to the bed 10. The computer 12 may be an IPAD or IPOD computer (by Apple Inc.), a TABLET computer (powered by ANDROID OS operating system), a PLAYBOOK computer (by BlackBerry), and/or other hand-held computers or displays (such as a television) with or without an accompanying touchscreen. The computer 12 has a central processing unit (CPU) that executes machine instructions, and a memory for storing the machine instructions that are to be executed by the CPU. As will be described in further detail, the computer 12 is programmed to facilitate in reorienting, decreasing anxiety, and/or reducing delirium risk in patients. As patients are sometimes unconscious while they are transported to the hospital, or after a medical procedure, or by virtue of their medical condition, patients can be very confused and disoriented when they wake up in a hospital bed. The patients can be anxious about their environment and current medical condition. The screen of the computer 12 faces the patient so that the computer 12 can reorient/calm the patient during periods of consciousness.

The computer 12 may be mounted to a connection member 14. The face of computer connection member 14 may be larger in length and width than the computer 12 that it holds. The computer connection member 14 may have a soothing color (e.g., soft blue) or shape (e.g., oval/rounded), so that when the patient awakes from unconsciousness the computer 12 is aesthetically pleasing and calming to the patient. In one embodiment, the connection member 14 is mounted to one end of a flexible arm 16. The flexible arm 16 is able to be bent and repositioned to a new shape, while rigid enough to maintain that shape. For example, the flexible arm 16 can be easily bent and rotated by the patient or another person so that the computer 12 is within or out of the patient's view and/or reach. In addition, the flexible arm 16 with the computer 12 can easily and quickly be moved to a position that could allow unobstructed routine and emergent care of the patient. An anchoring member 18 mounts the arm 16 to the bed 10, and is located on the opposite end of the arm 16 from the computer 12. The anchoring member 18 may be a removable and flexible C-clamp, O-clamp, or other attachment enabling the arm 16 to be efficiently removed from the hospital bed 10. The anchoring member 18 and attached arm 16 may be configured to be able to slide lengthwise along the hospital bed 10, as depicted in FIG. 1. The anchoring member 18 may alternatively be otherwise secured to the bed 10 so that the arm 16 is fixedly secured to the bed 10, or the arm 16 may be integrally formed with the bed 10.

Figure 2:
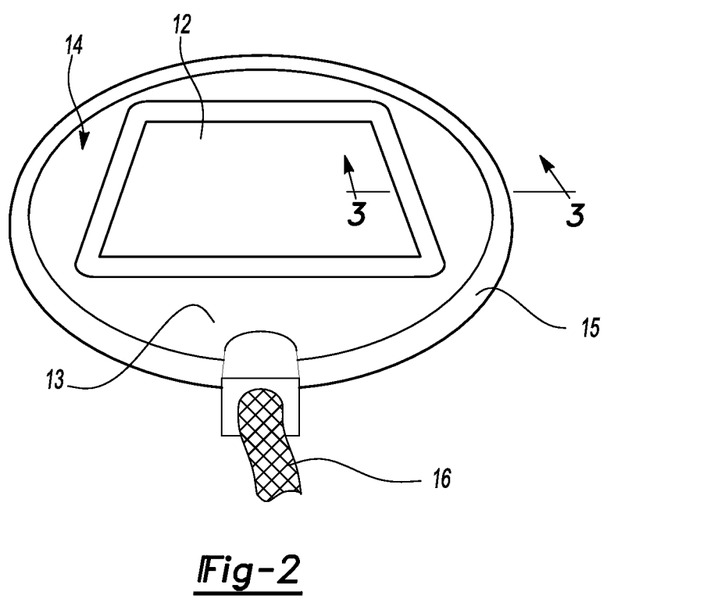
FIG. 2 is a perspective view of the computer of FIG. 1 mounted on a connection member at one end of the flexible arm according to one embodiment.
Figure 3:
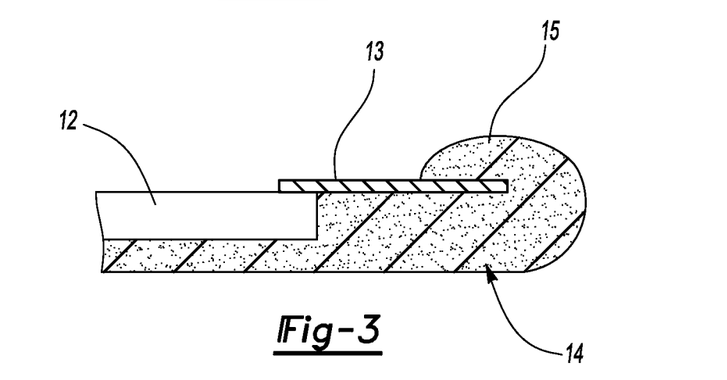
FIG. 3 is a cross-sectional, cut-away view of the computer and the connection member taken along line 3-3 in FIG. 2.

Referring to FIGS. 2 and 3, in one embodiment, the computer 12 is received within the connection member 14 and secured underneath a cover 13 which extends at least partially over the computer 12. For example, the cover 13 may extend over a frame portion of the computer 12 while allowing obstructed access to a screen portion of the computer 12. The cover 13 may be formed of transparent plastic or any other suitable material, and may be received under a lip 15 of the connection member 14 so as to secure the computer 12 to the connection member 14. Of course, other configurations for holding the cover 13 in position with respect to the connection member 14 are also contemplated, and it is also understood that cover 13 is not required. In another example, a sleeve or the like may be provided as a connection member 14 to receive the computer 12, such that in this case the face of the connection member 14 is substantially similar in length and width to the computer 12. Access ports (not shown) may be provided around the connection member 14 to allow access to different computer buttons or computer ports if needed. The arm 16 is attached to the connection member 14 and is described in further detail below.

Figure 4:
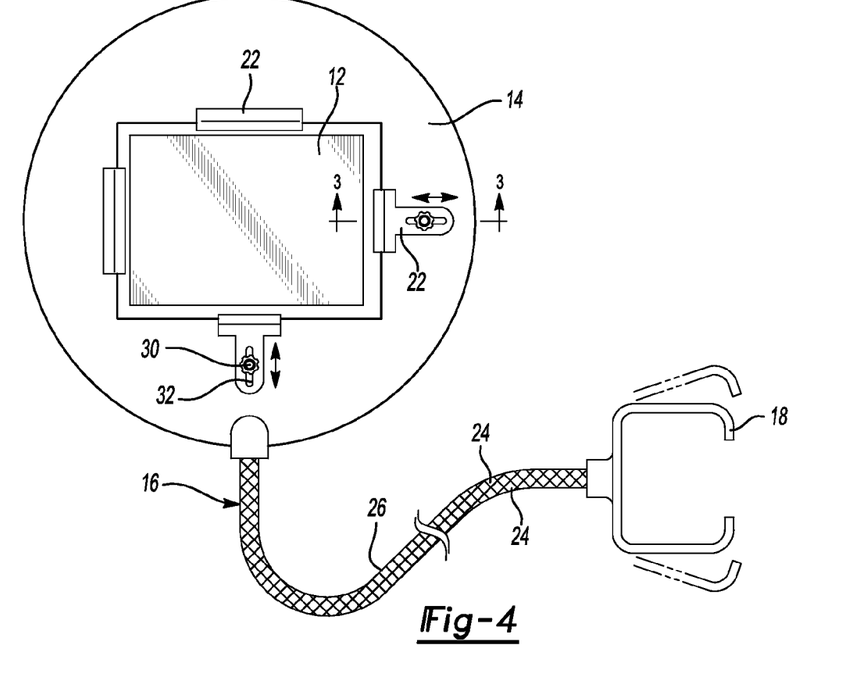
FIG. 4 is a plan view of the computer mounted on a connection member according to another embodiment, also depicting an anchoring member on the other end of the flexible arm that connects the arm to the bed.

Referring to FIG. 4, in another embodiment, computer fasteners 22 are shown disposed at positions around the perimeter of computer 12. The fasteners 22 are scalable vertically and horizontally, and attached to the connection member 14. This enables the fasteners 22 and connection member 14 to accommodate for various sizes and types of computers 12 as previously described. There may also be hook and loop or other fastening means to further or alternatively secure the computer 12 to the connection member 14.

The arm 16 may be made of a number of separate rotatable members 24. These members 24 may interlock with one another, and are each individually rotatable. The implementation of interlocking members 24 in a flexible arm 16 in a hospital room setting allows the computer 12 to be positioned in various angles and positions relative to the patient's hospital bed, and not merely limited to one or two axes of rotation. The computer 12 may be initially positioned in front of and above the patient, as illustrated in FIG. 1a, so that the computer 12 is one of the first items the patient sees when he becomes conscious. The computer 12 may subsequently be repositioned so that the computer 12 is not facing the patient, but rather facing a doctor or other third party to view and operate. Also, as the patient may later use the computer 12 while the patient is conscious, the flexible arm 16 allows the patient to reposition the computer 12 to multiple locations and distances from the patient's body (FIG. 1b). A sleeve 26 surrounds the outer portion of the interlocked members 24. Conductive wires (not shown) may be fed within the sleeve 26 so as to be hidden from plain view. The wires connect the computer 12 to a power source (not shown) through a wall outlet, for example.

Figure 5:
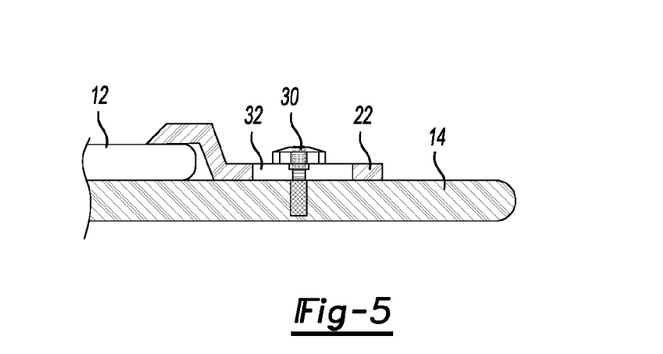
FIG. 5 is a cross-sectional, cut-away view of the computer and the connection member taken along line 5-5 in FIG. 4.

Referring to FIGS. 4 and 5, the scalable fasteners 22 are shown in detail. The scalability of the fasteners 22 may be accomplished by a bolt 30 and groove 32 combination. A bolt 30 is assembled through a groove 32 of the fastener 22, and into the connection member 14. When the bolt 30 is slightly loosened, the fasteners 22 can slide along the bolt 30 until a desired location is met, and the bolt 30 is tightened again to fix the fasteners 22 in place. Other scalable or slidable mechanisms known in the art may be substituted for the bolt 30 and groove 32 combination in order for the connection member 14 to accommodate various sizes and types of computers 12.

Figures 6A, 6B, 6C:
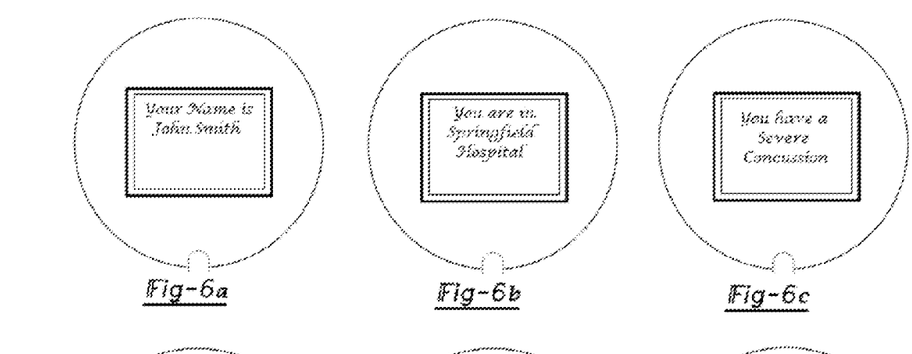
FIGS. 6a-f are screen shots of various example content pages displayed by the computer in which content is communicated from the CPU to the patient to help reorient and reduce anxiety in the patient.
Figures 6D, 6E, 6F:
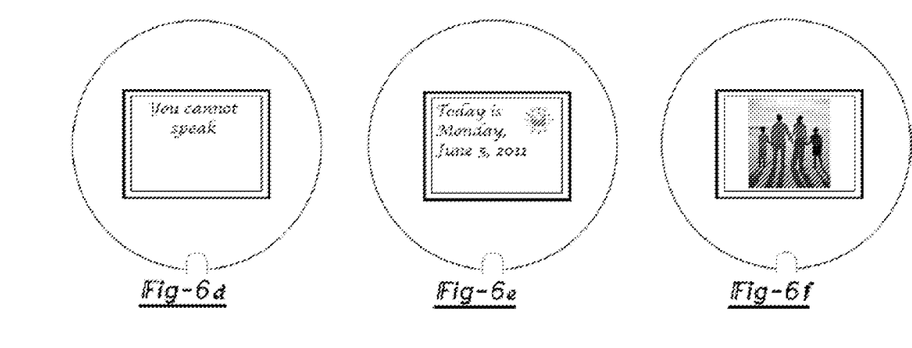
Figure 7A:
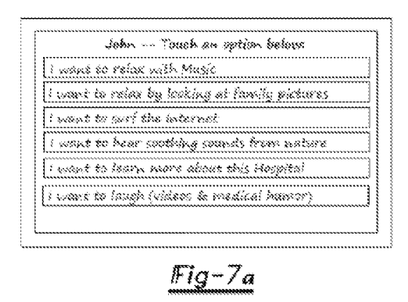
FIG. 7a is a screen shot of an interactive menu displayed by the computer operating an active module in which the CPU and the patient communicate interactively, the menu providing example activity options for the patient.
Figure 7B:
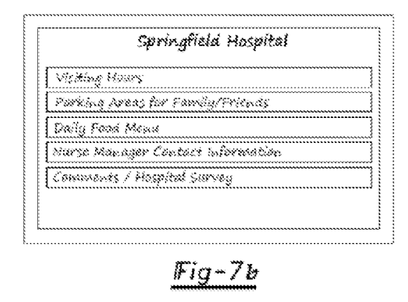
FIG. 7b is a screen shot of an interactive menu displayed by the computer operating in the active module, the menu providing example hospital information selections.
Figure 7C:
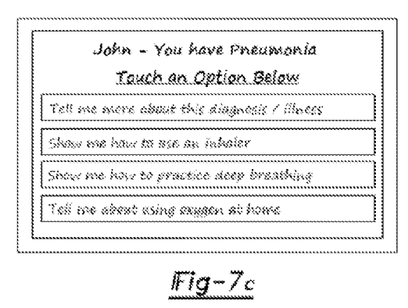
FIG. 7c is a screen shot of an interactive menu displayed by the computer operating in the active module, the menu providing example selections for a pneumonia diagnosis for the patient.
Figure 7D:
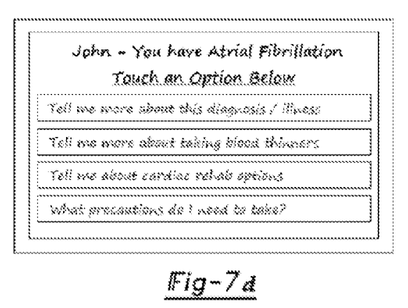
FIG. 7d is a screen shot of an interactive menu displayed by the computer operating in the active module, the menu providing example selections for an atrial fibrillation diagnosis for the patient.
Figure 7E:
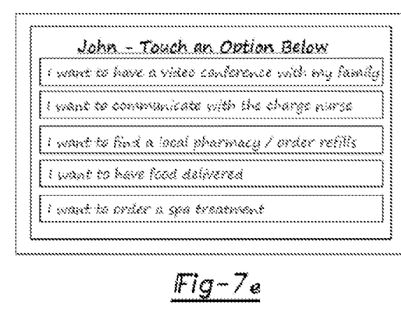
FIG. 7e is a screen shot of an interactive menu displayed by the computer operating in the active module, the menu providing example communication and activity selections for the patient.
Figure 8A:
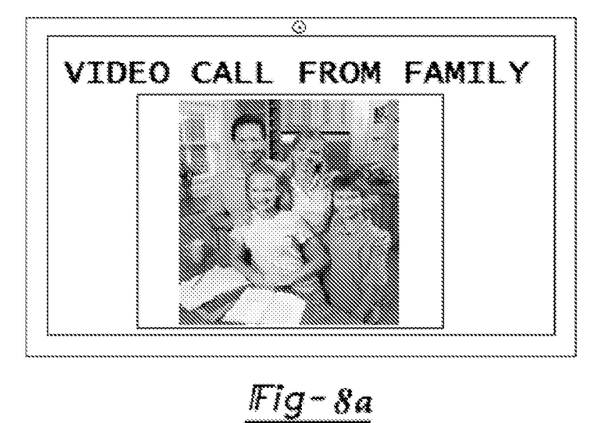
FIGS. 8a and 8b are screen shots of an example interface on the computer for a video call and video conference, respectively.
Figure 8B:
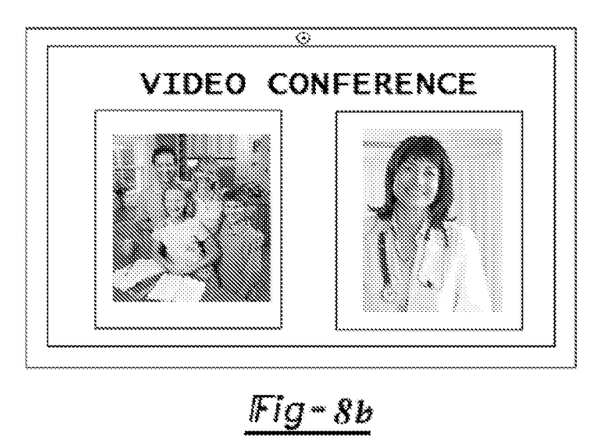

Referring to FIGS. 6-8, the computer 12 includes a program that may execute a passive module and/or an active module. These modules may be contained within an app that can downloaded from an electronic storefront including apps, such as the APP STORE by Apple Inc. It is understood that any operating system platform could be used to implement the passive and active modules. The passive module is illustrated in FIGS. 6a thru 6f. The passive module may initiate and operate while the patient is in the intensive care unit (ICU) or "step-down ICU" setting. Patients in these environments are sometimes streaming intermittently between unconscious and varying levels of consciousness. The patient may intermittently awaken for split second or longer. This patient may wonder, for example, "Where am I? What date is this? What season is this? Have I been unconscious for a long time? Am I in a coma? Why can't I speak? What is my condition? What happened to me? Where is my family? Does my family know I'm here?" During these brief conscious moments, there is often no same-language speaking nurse or medical staff personnel present at the bedside to provide answers to these potential questions. As a result, there is no consistent bedside method to help reduce anxiety and to assist with reorientation to the patient's name, hospital location, time, date, season, "non-speaking" status, and their current serious medical condition, for example. In addition, family members are often not available to constantly be at their bedside to help with this reorientation and anxiety-reducing process. As a result, the patient may feel alone, anxious and can become disoriented, confused, and/or can subsequently develop delirium. In addition, this psychological condition can produce physiological responses such as elevated heart rate, blood pressure and respiratory rate which can mislead medical staff caregivers that a change in medical condition has developed. Unfortunately, this potential misinterpretation can lead to the ordering of many emergency medical tests and medications that can have iatrogenic effects.

The passive module of computer operation is an aid to reorient and reduce anxiety until the patient regains full or partial consciousness, orientation, and a calm/non-anxious state. A doctor, nurse, or other caregiver may input some basic patient-specific information into the computer. This patient-specific information may include an identification of the patient (such as, but not limited to, the patient's name, age, and birthdate), the location of the patient (such as, but not limited to, the hospital name, city, and state), the diagnosis or medical status of the patient, and the native language that the patient speaks and reads. Other third parties, such as family members of the patient, may also send information to the computer, such as personal photographs, videos, or music. This can be accomplished by directly downloading the content from the internet to the computer, or by transferring the content onto the computer wirelessly through radio waves (e.g., BLUETOOTH/Wi-Fi).

The patient-specific content is received and processed by the CPU of the computer 12. Then, during the operation of the passive module, the computer 12 communicates to the patient by displaying this information on the computer screen. In one embodiment, the patient-specific content is native language-specific. The information may be displayed on a single content page or throughout multiple content pages, as shown in FIGS. 6a thru 6f. FIG. 6a shows the computer 12 displaying the patient's name. FIG. 6b shows the computer 12 displaying the physical location of the patient. In FIG. 6c, the computer 12 displays the medical status of patient as diagnosed by the doctor, such as "You have a severe concussion," or "You have pneumonia." Certain other important and specific information is displayed in FIG. 6d, such as "You cannot speak," or "You are on a respirator," or "Your family is on their way." In FIG. 6e, the computer displays the current date, and may also display the day and time. For example, the passive module may indicate the general or specific time of day (e.g., with a sun or moon icon, such as shown in FIG. 6e, or with an actual a.m. or p.m. time) in an effort to help establish day/night cycle orientation for the patient. FIG. 6f shows the computer displaying a personalized family photograph uploaded onto the computer from the doctor, a family member, or some other third party. It should be understood that the content and order of these Figures are merely exemplary, and more or less patient-specific content or a different order may be used; these are examples of content pages that are helpful for reorienting and reducing anxiety until a patient regains partial or full consciousness, orientation, and a calm/non-anxious state. In addition, the order in which the content pages are displayed can be customized and selected by a caregiver.

As described, the patient-specific content may be displayed throughout multiple content pages on the screen. These content pages may be looped in a continuous loop. As it is unpredictable when many patients will regain consciousness, the continuous loop assures that at any point of the loop the patient may be reoriented and have his/her anxiety reduced until the patient regains full or partial consciousness, orientation, and/or a calm/non-anxious state. For example, in one embodiment, the entire loop is about two minutes long. Within the "app" or passive module, this time is adjustable to a longer or shorter time, depending on the condition of the patient. If, for example, the patient is in and out of consciousness/alertness, each content page may be displayed for a longer period of time to decrease the speed of the content page revolution in the loop. In this fashion, the computer system can better attempt to reorient the patient by allowing him to focus on a particular content page and process the information presented for the short period until the patient has regained consciousness with a higher level of alertness and less anxious state. Each content page may alternatively be displayed for a shorter amount of time, such as when the patient is conscious for longer periods of time. The duration of each content page may also be customized, such that certain content pages may have longer dwell times than others, perhaps depending on the type or amount of information presented on a particular content page. Visual aids may be provided for patients with poor sight capabilities.

Often, due to various hospital environments and other factors, hospitalized patients may not be oriented to day and night hours. As a result, the day and night sleep cycle may be shifted leading to potentially anxiety and delirium. One embodiment, would be have a "daytime program" with, but not limited to, awakening sounds, or brighter video images/cues to establish daytime orientation Likewise, a "nighttime program" with soothing sounds and dimmer video images/sequences can be automatically programmed. By reestablishing, appropriate day and night cycles, anxiety and delirium can potentially be reduced. This can be implemented automatically within the active module.

Audio may also be provided that corresponds to the loop of content pages. For example, spoken words may read what is shown on the screen of the computer 12. In one embodiment, the audio is selected to be in the native language of the patient. The audio may be directly output by the computer 12 through its own internal speakers, or the audio may be output to external speakers or stereo wireless/BLUETOOTH headphones placed on the patient. The audio may also be in a soothing voice tone. This may further reorient the patient and reduce anxiety, especially while the patient is semi-conscious or otherwise unable to focus or see computer 12 clearly. In addition, calm music (i.e., waterfall, ocean waves, etc.) may stream continuously through stereo wireless headphones, facilitating decreased anxiety. Other music selections such as, for example, native ethnic music can also be provided for selection by a caregiver or other user. Noise cancellation "sound sequence" programs can also be implemented. This music/sound stream will help to block ambient noise in the ICU or other hospital units and facilitate the reorienting process.

If a patient improves in the ICU or other medical floor, the patient can potentially become more interactive with their environment and staff. At this point, the patient can be fully aware and cooperative with others. Unfortunately, many illnesses and just being in a hospital setting can lead to an anxious or even depressed mood. Often patients are spending countless hours waiting for tests to be done. Without connections to the outside the hospital environment, patients can become bored, isolated, and detached.

Under such circumstances, the computer 12 may execute an active module rather than the passive module. The active module and the passive module can either be independent of each other or packaged together, and these modules can be contained within an app that can downloaded from an electronic storefront including apps, such as the APP STORE from Apple Inc. The functional switch from the passive module to the active module may be implemented by a nurse, for example. The patient may rotate the computer 12 and the flexible arm 16 so that the patient may utilize the touch screen on the computer 12. Throughout the operation of the active module, the patient's touch and interactive input plays a role in the process of reducing anxiety, depressed mood, and boredom. The active module also begins to take a role of a concierge-type service.

Referring to FIGS. 7a-7e and 8, the computer 12 is shown operating the active module. In FIG. 7a, the computer 12 displays an interactive menu from which the patient can choose options. For instance, the touch-screen of the computer 12 may provide the patient with the options to relax by listening to music, to listen to soothing sounds from nature (e.g., waves at the beach), or to look at pictures. The patient may also be able to choose to surf the internet, browse online videos, or learn more about the hospital in which the patient is located (FIG. 7b). Due to a patient potentially feeling depressed about their condition, integrated or links to comedy vignettes can help to uplift patient spirits and detract from their illness.

As illustrated in FIGS. 7c and 7d, the patient may be able to direct the interactive menu to instruct the computer 12 to show information about his/her own condition. Videos of the patient's personal illness, the side effects, and other treatment information may be at the viewing control of the patient. "On-demand" patient-specific educational videos may also be selected by the patient. Some examples include, but are not limited to, how to use an asthma inhaler, how to administer insulin, how to take warfarin/coumadin, etc. Current television or education videos in the hospital are not "on demand" and do not often coincide to when a patient is available to watch in their hospital room. As shown in FIG. 7e, the patient may also learn more about the food and pharmaceutical stores in the surrounding area outside of the particular hospital. This can function as a concierge-type service—for example, the patient can potentially quickly order a pizza or anxiety—reducing spa services that can be performed in the hospital room. In addition, the patient can find a local drug store that can fill the patient's prescriptions when leaving the hospital. This information can be relayed to family members to aid in the patient's health care recovery. This is also an avenue by which businesses can advertise their services to the patient and his/her family.

Often, many family members are not able to visit their loved ones in the hospital due to geographic differences. For example, a close family member in California may not be able to directly speak or visualize the condition of the patient in Michigan. As a result, medical decision making may not be optimal without a family member able to aid in this process. Accordingly, with reference to FIGS. 7e and 8, one embodiment of the active module in computer 12 may implement a "video cam" function that would allow the patient to interact visually with a next of kin/other family member to guide medical decision making. In addition, medical care personnel would also be able initiate a video conference with a geographically remote durable power of attorney/legal guardian with the patient and physicians/nurses at the patient bedside. Currently, this mode of communication between the patient and his/her family members and medical personnel is not readily available or utilized. In one embodiment, a specific app/source code within the iOS (Apple Inc.) called FACETIME app could facilitate this two way video conference interaction between an IPAD/IPOD computer and be implemented within the active module. Such a module integrated and interactive capability may serve to decrease a patient's anxiety when making important end of life or other serious decisions regarding a patient's health.

FIGS. 6-8 do not depict an exhaustive list of content or options available to the patient. For example, the patient may also be able to play a game or select a different language for the computer 12 to communicate with the patient. The patient may also select an option that displays a "virtual nurse" that can direct the patient to information about his/her condition in a personal way or to guide the patient on how to use and interact with the active module and system. It is understood that content described with reference to the passive or active module may be appropriate for use with the other, and the active module may also display patient-specific information from the passive module in an appropriate format, such as adjacent menu options. After choosing any of the options available, the patient may return to the interactive menu by simply pressing an on-screen button that directs the computer 12 back to the menu.

A computer system with an active module, such as the system described herein, may aid the patient to a more rapid recovery. The interaction between the computer 12 and the patient allows the patient to not only decrease anxiety, but also serves to increase patient satisfaction for their "consumer experience" in the hospital. This can lead to more patient loyalty to a particular hospital. Local restaurants and stores can advertise for their services through the computer 12. For example, the patient may look at the map of the surrounding areas, and the local businesses may advertise by placing their logo on their corresponding location on the map with a web link. The above features implemented within the active module can offer concierge-type consumer experience for the patient and his/her family while the patient is still hospitalized.

In one embodiment, a database server and database (not shown) may also be provided. The database server is adapted to communicate with multiple computers 12 and CPUs within the hospital. Each computer 12 is given its own identification so that the server can directly communicate with each dedicated computer 12 individually. This provides the hospital with the ability to better manage each computer's content from one location. For example, hospital employees, may input and transmit patient-specific content to the database, which then transmits the content to the corresponding computer 12 associated with the specified patient. Other permitted remote users, such as family members of patients, may be given the ability to access the database server remotely, and upload pictures, messages, videos, or audio files to the server. The server then transmits this data to the patient's specific computer for the patient to access during use of the active or passive module. Remote users may be given a password that allows them to access a limited portion of the database so that the remote users can only send content to the designated computer that is used by the intended recipient patient. Peer-to-peer sharing of content between computers 12, such as for transferring patient-specific content between computers 12 when a patient is moved between the ICU, step-down ICU/ progressive care units, general medical floor is also contemplated.

While exemplary embodiments are described above, it is not intended that these embodiments describe all possible forms of the disclosure. Rather, the words used in the specification are words of description rather than limitation, and it is understood that various changes may be made without departing from the spirit and scope of the disclosure. Additionally, the features of various implementing embodiments may be combined to form further embodiments of the disclosure.

What is claimed is:

1. A computer system for reorienting, reducing anxiety and/or reducing risk factors for delirium in a patient in a medical facility comprising a computer having a central processing unit (CPU) for executing machine instructions comprising a passive module and a memory for storing machine instructions that are to be executed by the CPU, the machine instructions when executed by the CPU implementing the following functions:
   receiving patient-specific content and non-patient-specific content;
   formatting the patient-specific content and non-patient-specific content into a series of content pages to form a looped content segment, the series of content pages including first, second and third reorientation messages based on the patient-specific content and non-patient-specific content, one of the first, second or third reorientation messages includes an identification of the patient, another of the first, second or third reorientation messages includes the facility name, and the remaining of the first, second or third reorientation messages includes the current time or date; and
   continuously looping the looped content segment for sequential display of the first, second and third patient reorientation messages to the patient.

2. The computer system of claim 1, wherein at least one other message is interspersed among the first, second and third reorientation messages.

3. The computer system of claim 1, wherein the first reorientation message includes the identification of the patient, the second reorientation message includes the facility name, and the third reorientation message includes the current time or date.

4. The computer system of claim 1, wherein the display of the looped content segment is selectable in the native language of the patient.

5. The computer system of claim 1, wherein the patient-specific content includes a digital picture of the patient.

6. The computer system of claim 1, wherein the looped content segment includes audio content.

7. The computer system of claim 1, wherein the looped content segment includes video content.

8. The computer system of claim 1, wherein the series of content pages includes a fourth reorientation message including a patient medical condition that is displayed last in the sequence of the looped content segment.

9. The computer system of claim 1, further comprising an active module in which the CPU and the patient communicate interactively, the machine instructions when executed by the CPU implementing the following functions of the active module:
   transmitting an interactive menu,
   receiving a selection on the interactive menu from the patient, and
   transmitting content corresponding to the selection to communicate interactively with the patient.

10. The computer system of claim 9, wherein the interactive menu includes an option for the patient to view photographs.

11. The computer system of claim 9, wherein the interactive menu includes an option for the patient to listen to audio content.

12. The computer system of claim 11, wherein the audio content is transmitted to a wireless headset.

13. The computer system of claim 9, wherein the interactive menu includes an option for the patient to conduct a video conference.

14. The computer system of claim 9, wherein the interactive menu includes an option for the patient to select "on demand" videos.

15. The computer system of claim 9, wherein the interactive menu includes advertisements that correspond to the selected content.

16. The computer system of claim 9, wherein the interactive menu includes hospital information.

17. The computer system of claim 9, wherein the interactive menu includes at least a portion of the patient-specific content.

18. The computer system of claim 1, further comprising a database server adapted to communicate with the CPU, wherein the database server receives patient-specific content.

19. A computer system for reorienting, reducing anxiety and/or reducing risk factors for delirium in a patient in a medical facility comprising a computer having a central processing unit (CPU) for executing machine instructions comprising a passive module and a memory for storing machine instructions that are to be executed by the CPU, the machine instructions when executed by the CPU implementing the following functions:

receiving patient-specific content including the patient's name and non-patient-specific content including the facility name housing the patient and the current time or date;

formatting the patient-specific content and non-patient-specific content into a series of reorientation content pages to form a looped content segment, ; and     continuously looping the looped content segment for sequential display of the series of reorientation content pages to the patient.

20. A computer system for reorienting, reducing anxiety and/or reducing risk factors for delirium in a patient in a medical facility comprising a computer having a central processing unit (CPU) for executing machine instructions comprising a passive module and a memory for storing machine instructions that are to be executed by the CPU, the machine instructions when executed by the CPU implementing the following functions:

receiving patient-specific content and non-patient-specific content;

formatting the patient-specific content and non-patient-specific content into a series of content pages to form a looped content segment, the series of content pages including first, second, third and fourth reorientation messages based on the patient-specific content and non-patient-specific content, one of the first, second or third reorientation messages includes an identification of the patient, another of the first, second or third reorientation messages includes the facility name, and the remaining of the first, second or third reorientation messages includes the current time or date; and     continuously looping the looped content segment for sequential display of the first, second, third and fourth patient reorientation messages to the patient.

\* \* \* \* \*